(12) United States Patent
Baptista et al.

(10) Patent No.: US 9,513,194 B2
(45) Date of Patent: Dec. 6, 2016

(54) AQUATIC MACROINVERTEBRATE SUBSAMPLING EQUIPMENT

(75) Inventors: Darcilio Fernandes Baptista, Rio de Janeiro (BR); Riccardo Mugnai, Rio de Janeiro (BR); Renata Bley De Oliveira, Rio de Janeiro (BR)

(73) Assignee: Fundação Oswaldo Cruz, Rio de Janeiro (BR)

( * ) Notice: Subject to any disclaimer, the term of this patent is extended or adjusted under 35 U.S.C. 154(b) by 449 days.

(21) Appl. No.: 13/698,278

(22) PCT Filed: May 18, 2011

(86) PCT No.: PCT/BR2011/000144
§ 371 (c)(1),
(2), (4) Date: Dec. 12, 2012

(87) PCT Pub. No.: WO2011/143730
PCT Pub. Date: Nov. 24, 2011

(65) Prior Publication Data
US 2013/0104674 A1    May 2, 2013

(30) Foreign Application Priority Data

May 19, 2010 (BR) .................................. 1003910

(51) Int. Cl.
| | | |
|---|---|---|
| G01N 1/22 | (2006.01) |
| G01N 1/10 | (2006.01) |
| G01N 1/12 | (2006.01) |
| G01N 1/18 | (2006.01) |
| G01N 33/18 | (2006.01) |
| A01K 61/00 | (2006.01) |

(52) U.S. Cl.
CPC ............... *G01N 1/10* (2013.01); *A01K 61/001* (2013.01); *G01N 1/12* (2013.01); *G01N 1/18* (2013.01); *G01N 33/186* (2013.01); *G01N 2001/1012* (2013.01)

(58) Field of Classification Search
CPC .. G01N 1/2205; G01N 1/10; B01L 2300/0681
USPC ....................................................... 73/863.23
See application file for complete search history.

(56) References Cited

U.S. PATENT DOCUMENTS

| 6,442,889 B1 | 9/2002 | Lee | |
| 7,205,016 B2 * | 4/2007 | Garwood | ...................... 426/108 |
| 2010/0189598 A1 * | 7/2010 | Fraundorfer | .................... 422/28 |

FOREIGN PATENT DOCUMENTS

IE           990858 A2        4/2001

OTHER PUBLICATIONS

International Search Report for PCT/BR2011/000144 dated Aug. 30, 2011.

* cited by examiner

*Primary Examiner* — John Fitzgerald
*Assistant Examiner* — Rodney T Frank
(74) *Attorney, Agent, or Firm* — Caesar Rivise, PC (57) ABSTRACT

The present invention refers to the subsampler and to a subsampling method that allows for the execution of environmental monitoring without the use of large sample volumes, thus ensuring specimen wealth and expedited analyses.

4 Claims, 7 Drawing Sheets

AQUATIC MACROINVERTEBRATE SUBSAMPLING EQUIPMENT

FIELD OF THE INVENTION

The present invention refers to the subsampler and to a subsampling method that allows for an environmental biomonitoring without the use of large sample volumes, thus ensuring the diversity of the species and a quick analysis.

BACKGROUND OF THE INVENTION

Biological monitoring is a core element in the water resource management and in the conservation of ecological integrity in water ecosystems (Karr, J. R. 1991. Biological integrity: a long-neglected aspect of water resource management. Ecological Applications, 1: 66-84; Rosenberg, D. M., and Resh V. H. (Eds.). 1993. Freshwater biomonitoring and benthic macroinvertebrates. Chapman and Hall (Eds.), New York, 488p; Karr, J. R., and Chu, E. W. 1999. Restoring Life in Running Waters: Better Biological Monitoring. Island Press, Washington, D.C.).

Biological water ecosystem monitoring programs were created in the early XX century by KOLKWITZ & MARSSON ([Kolkwitz, R., and Marsson, M. 1908. Ökologie der pflanzlichen Saprobien. Bericht der Deutschen Botanischen Gesellschaft 26a: 505-519. (Translated 1967). Ecology of plant saprobia. In Kemp, L. E., W. M. Ingram & K. M. Mackenthum (eds), Biology of Water Pollution. Federal Water Pollution Control Administration, Washington, D.C.: 47-52.] [Kolkwitz, R., and Marsson, M. 1909. Ökologie der tierischen Saprobien. Beiträge zur Lehre von des biologischen Gewasserbeurteilung. Internationale Revue der gesamten Hydrobiologie und Hydrographie, 2: 126-152.]), which set the conceptual foundations for the construction of biomonitoring methods.

From their inception to the end of the 1980s, biotic indices predominated as biological monitoring tools ([Metcalfe, J. L. 1989. Biological Water Quality Assessment of Running Waters Based on Macroinvertebrate Communities: History and Present Status in Europe. Environmental Pollution, 60: 101-139.]; [Rosenberg, D. M., and Resh V. H. (Eds.). 1993. Freshwater biomonitoring and benthic macroinvertebrates. Chapman and Hall (Eds.), New York, 488p)].

More recently, new approaches were set as tools for biomonitoring such as predictive models (RIVPACS—UK; AusRivAs—Australia; BEAST—Canada, New Zealand model) (Wright, J. F. 1995. Development and use of a system for predicting the macroinvertebrate fauna in flowing waters. Australian Journal of Ecology 20: 181-197; Norris, R. H., and Georges, A. 1993. Analysis and interpretation of benthic macroinvertebrate surveys. Chapman and Hall, New York (USA), pp. 234-286. 1993; Reynoldson, T. B.; Bailey, R. C; Day, K. E., and Norris, R. H. 1995. Biological guidelines for freshwater sediment based on Benthic Assessment of SedimenT (the BEAST) using a multivariate approach for predicting biological state. Australian Journal of Ecology 20:198-219; Joy, M. K., and Death, R. G. 2003. Biological assessment of rivers in the Manawatu-Wanganui region of New Zealand using a predicative macroinvertebrate model. New Zealand Journal of Marine and Freshwater Research 37: 367-379).

The development of multimetric indices has been prioritized in the US since the late 1980s ([Plafkin, J. L.; Barbour, M. T.; Porter, K. D.; Gross, S. K., and Hudges R. M. 1989. Rapid bioassessment protocols for use in sites and rivers: Benthic macroivertebrates and fish. U.S. Environmental Protection Agency, EPA, 444/4-89-001, Washington, D.C.], [Barbour, M. T.; Gerritsen, J.; Griffith, G. E.; Frydenborg, R.; McCarron, E.; White, J. S., and Bastian, M. l. 1996. A framework for biological criteria for Florida streams using macroinvertebrates. Journal of North American Benthology Society. 15 (2), 185-211]; [Barbour, M. T.; Stribling, J. B., and Karr, J. R. 1995. The multimetric approach for establishing biocriteria and measuring biological condition. Pp: 63-76. In: Davis, W. & Simon, T. (eds). Biological Assessment and Criteria: Tools for Water Resource Planning and Decision Making.] [Lewis Publishers. Ann Arbor, Mich.; Barbour, M. T.; Gerritsen, J.; Griffith, G. E; Frydenborg, R.; McCarron, E.; White, J. S., and Bastian, M. L. 1996. A framework for biological criteria for Florida sites using benthic macroinvertebrates. J. N. Am. Benthol. Soc, 15(2): 185-211)]; [Gibson, G. R.; Barbour, M. T.; Stribling, J. B.; Gerritsen, J., and Karr, J. R. 1996. Biological Criteria. Technical Guidance for Sites and Small Rivers. EPA/822-B-96-001. U.S. Environmental Protection Agency. Office of Science and Technology, Washington, D.C.]). European Union countries recently started to invest in the standardization and use of multimetric indices, following the proposals set by the Water Framework Directive No. 2000/60/EC (EC, 2000 European Commission. The EU Water Framework Directive—Integrated River Basin Management for Europe. Available at: http://ec.europa.eu/environment/water/water-framework/index_en.html accessed on: Feb. 21, 2008.). In this sense the EU produced the AQEM and STAR projects to standardize and inter-calibrate the operating procedures and development of different multimetric indices, based on the fauna of macroinvertebrates (Pinto P.; Rosado, J.; Morais, M., and Antunes, I. 2004). Assessment methodology for southern siliceous basins in Portugal. Hydrobiology, 516: 193-216; Bohmer, J.; Rawer-Jost, C, and Zenker, A. 2004. Multimetric assessment of data provided by water managers from Germany: assessment of several different types of stressors with macrozoobenthos communities. Hydrobiologia, 516: 215-228; Vlek, H. E.; Verdonschot, P. F. M., and Nijboer, R. C. 2004. Toward a multimetric index for assessment of Dutch stream using benthic macroinvertebrates. Hydrobiologia, 516: 173-189; Buffagni, A.; Erba, S.; Cazzola, M., and Kemp, L. L. 2004. The AQEM multimetric system for the southern Italian Alpennines: assessing the impact of water quality and habitat degradation on pool macroinvertebrates in Mediterranean rivers. Hydrobiologia, 516: 313-329; Furse, M. T.; Hering, D.; Brabec, K; Buffagni A.; Sandin, L., and Verdonschot, P. F. M. 2006. The Ecological Status of European Rivers: Evaluation and Intercalibration of Assessment Methods. Hydrobiologia, 566: 3-29).

The strength of the multimetric approach lies in the ability to integrate data from the various aspects of a community to provide a general classification of the level of degradation in an ecosystem without losing information from individual metrics. The metrics should be based on solid ecological concepts and represent complex ecosystem processes, to allow for the assessment of ecological functions. The use of different nature metrics may allow for a qualitative evaluation, in addition to the quantitative one, as a metrics may, individually, be able to qualify the source of the impact.

In general, all of the indices were initially formulated considering exhaustive collection and separation work in the surveying of the macroinvertebrate benthic fauna. Therefore, the indices are constructed considering a biological database that is very robust but with limited application in routine procedures.

From a practical standpoint, following the collection procedure, all the substrates sampled, organic materials (leaves/algae/macrophytes) and minerals (silt, sand, fine rock, stones) are transported to the laboratory and washed and after that the separation and identification of the biological material are initiated; it should be highlighted that the volume of raw material collected can reach up to 15-20 liters. Among the disadvantages of these techniques we could point the large volumes of the samples collected that have to be correctly treated and stored, the time spent in separating the substrate and the sizable amount of hours spent in the identification of all the specimens, apart from the large quantity of alcohol used in the preservation of the material. We should also point that the number of specimens collected frequently reaches thousands of larvae, which considerably increases operating costs and the environmental impact.

In this context quick evaluation protocols are being developed as simple tools and with low application costs, to assess the health of water ecosystems. These protocols blend simple and cost-effective field equipment with an optimized processing of the samples in the lab.

Subsampling is a technique currently used in Europe and in the US, consisting of counting and identifying a part of the randomly obtained community in the total sample collected in the field. The goal of subsampling is to generate a faithful and unbiased representation of a larger sample. It should be random and incorporate the heterogeneous character and diversity of the habitats studied in the field. This leads to a reduction of the effort required.

With this system, all the material collected is taken to the lab, washed and mixed through different techniques, allowing it to become homogeneous. Through a subsampler (tray split into 24 areas) one randomly chooses a portion of the sample Quick evaluation protocols produced in the US ([Plafkin, J. L.; Barbour, M. T.; Porter, K. D.; Gross, S. K., and Hudges R. M. 1989. Rapid bioassessment protocols for use in sites and rivers: Benthic macroinvertebrates and fish. U.S. Environmental Protection Agency, EPA, 444/4-89-001, Washington, D.C.], [Barbour, M. T.; Gerritsen, J.; Snyder, B. D.; and Stribling, J. B. 1999. Rapid Bioassessment Protocols for Use in Sites and Rivers: Periphyton, Benthic Macroinvertebrates and Fish, Second Edition. EPA 841-B-99-002. The US Environmental Protection Agency; Office of Water; Washington, D.C.]) traditionally recommend subsampling via counting of a fixed number. In these protocols the minimum number of organisms recommended to ensure efficiency in evaluation is of at least 300 individuals; in order to prevent much instability in the index metrics and provide reliable results for the evaluation. In practical terms, however, there is a big variation in the minimum number of organisms counted, depending on the analysis at hand. Additionally, when comparing the number of subsamples, it is possible to see the frailty in the small amount of samples.

Another type of subsampling is that done per area which is also the standard procedure suggested by the AQEM. This protocol suggests the use of trays split into quadrats where 25% of the total sample, of a minimum 300 individuals, are sorted. Area subsampling guarantees the random nature of the procedure, making it less subjective and less prone to the variations inherent to team change. However, there are still problems related to the large volume of the samples collected, to their storage, conservation, separation from the substrate, amount of alcohol used, and the quantity of specimens collected, that can reach thousands of individuals, amongst larvae and adults.

Regardless of the kind of sampling, the existing state-of-the-art methods have been discussed in several studies in countries where biomonitoring programs are already in application (EU, Australia and the US) ([Barbour, M. T.; Gerritsen, J.; Griffith, G. E.; Frydenborg, R.; McCarron, E.; White, J. S., and Bastian, M. 1. 1996. A framework for biological criteria for Florida streams using macroinvertebrates. Journal of North American Benthology Society. 15 (2), 185-211]; [Countermanch, D. L. 1996. Commentary on the subsampling procedures used for rapid bioassessments. Journal of North American Benthological Society 15: 381-385]; [Somers, K. M.; Reid, R. A., and S. M. 1998. Rapid ecological assessment: how many animals are enough. Journal of the North American Benthological Society 17: 348-358.]; [Doberstein, C. P.; Karr, J. R.; Conguest, L. L. 2000. The effect of fixed-count subsampling on macroinvertebrate biomonitoring in small streams. *Freshwater Biology*, Volume 44 (2): 355-371]; [Lorenz, A.; Hering, D.; Feld, C, and Rolauffs, P. 2004. A new method for assessing the impact of hydromorphological degradation on the macroinvertebrate fauna of five German stream types. Hydrobiologia, 516: 107-127]).

One of the biggest issues associated with biosampling is that of the wealth of species. The number of taxa found in a sample increases asymptotically as a function of the area sampled and of the number of individuals in the sample. Thus, it is always expected that, with the increase in the effort, one would obtain a greater wealth of species. The issue to focus on, in the specific case of subsampling for biomonitoring is that when this increase no longer is significant and, at the same time, provides an explanation for the change in ecosystem integrity. Apart from that, the full processing of this type of sample, with many individuals, is too costly.

Thus, the state-of-the-art is embedded with the issue is of how to carry out the subsampling and what the optimal effort is, in the sense of speeding the evaluation without impairing the ecological validity of the response ([Barbour, M. T.; Gerritsen, J.; Griffith, G. E; Frydenborg, R.; McCarron, E.; White, J. S., and Bastian, M. L. 1996. A framework for biological criteria for Florida sites using benthic macroinvertebrates. J. N. Am. Benthol. Soc, 15(2): 185-211]; [Countermanch, D. L. 1996. Commentary on the subsampling procedures used for rapid bioassessments. Journal of North American Benthological Society 15: 381-385]; [Doberstein, C P.; Karr, J. R.; Conguest, L. L. 2000. The effect of fixed-count subsampling on macroinvertebrate biomonitoring in small streams. *Freshwater Biology*, Volume 44 (2): 355-371]; [Nichols, S. e Norris, R. H. 2006. River condition assessment may depend on the sub-sampling method: field live-sort versus laboratory sub-sampling of invertebrates for bioassessment. Hydrobiologia, 572: 195-213]). The subsampling should preferably be carried out in the field or, better yet, in the laboratory.

Clarke and collaborators (2006) (Clarke, R T.; Furse, M T.; Gunn, R. J. M.; Winder, J. M., and Wright, J. F. 2002. Sampling variation in macroinvertebrate data and implication for river quality indices, Freshwater Biology 47: 1735-1751) studied the effect of subsampling directly on the metrics of different types and found that the precision of the measurements based on the wealth of taxa is quite affected by the size of the subsample, which is predictable due to the species-area ratio.

Apart from the analysis of the sampling effort, it is always necessary to verify if the subsampling apparatus guarantees the randomization of the organisms, that is, that the organisms are in a given quadrat by chance. A trend observed in this stage can lead to errors in determining the minimum evaluation effort and, in the context of a biomonitoring program, errors in the evaluation of ecological integrity. In biological terms, it is necessary to ask whether the organisms are randomly distributed in the space, or in this case, in the subsampling tray. If the random pattern indeed exists, the Poisson distribution is the right statistical descriptor for the data (Krebs, C. J. 1998. Ecological Methodology. Benjamin/Cummings, Menlo Park.). The Poisson distribution assumes that the expected number of organisms of a particular taxon is the same in all the quadrats and is equal to the population average, estimated based on the sampling average.

In this context, several subsamplers are found in the state-of-the-art. They basically consist of a plastic tray split into 24 areas. This equipment allows for the reduction of relative time in substrate separation and fauna identification, but does not solve the issues related to the large volume of samples collected, their storage, conservation, amount of alcohol used and the number of specimens collected. However, on the other hand, they produce damage to the specimens as a result of the homogenizing process that hamper the separation and identification, apart from not contributing to the preservation of the biota.

It is important to point that, if time and resource-saving procedures such as subsampling are applied to the biological monitoring with no prior analysis for equipment accuracy and precision, as well as methods used, the data collected could be useless, resulting in waste of resources, or even in the misled application of handling measures. On the other hand, the application of exhaustive procedures that use much lab time and resources, taking long to provide the biological answer are not practical in terms of application of biomonitoring programs that should assess the condition of hundreds of water bodies. Thus, equipment and methodologies are needed that would allow for an ideal cost-benefit ratio, ensuring the applicability of the tool, without the loss of scientific rigor and power to inference and decision.

This way, the creation of new subsampling equipment and methodologies that gather the usability features for small volumes, random distribution of the fauna, maintenance of their integrity, and environmental respect, are needed.

SUMMARY OF THE INVENTION

The goal of the present invention is to carry out the biomonitoring of water bodies without the technical limitations of the methodologies and of the subsamplers as found in the state-of-the-art.

The first achievement of the present invention refers to a subsampler that allows the carrying out of environmental monitoring without the use of large sample volumes, thus ensuring specimen wealth and speed in the analysis. The Subsampler in the present invention consists of a set of independent structures: two trays, a separator, and support legs. The equipment also presents a measurement system for its correct positioning on site and packaging and transport systems. The subsampler, unlike the others, is preferably used directly in the field. As an alternative, the equipment can also be used in the laboratory, fully assembled or on a benchtop if without the legs.

A second achievement of the present invention relates to the subsampling methodology. It consists of correctly positioning the subsampler of this invention on the surface; adding the substrate collected in the water medium onto the internal tray; removing the large-sized material, draining part of the water through the opening of the water drain system without fully removing it, adding the anesthetic solution so that the organisms found there reduce their moving capacity, homogenizing the substrate, fitting the separator onto the internal tray, opening the water drain flow system to discharge the anesthetic solution, randomly removing the substrate from the chosen quadrats, storing the removed substrate in alcohol and transporting it to the laboratory.

DETAILED DESCRIPTION OF INVENTION

Figure 1:
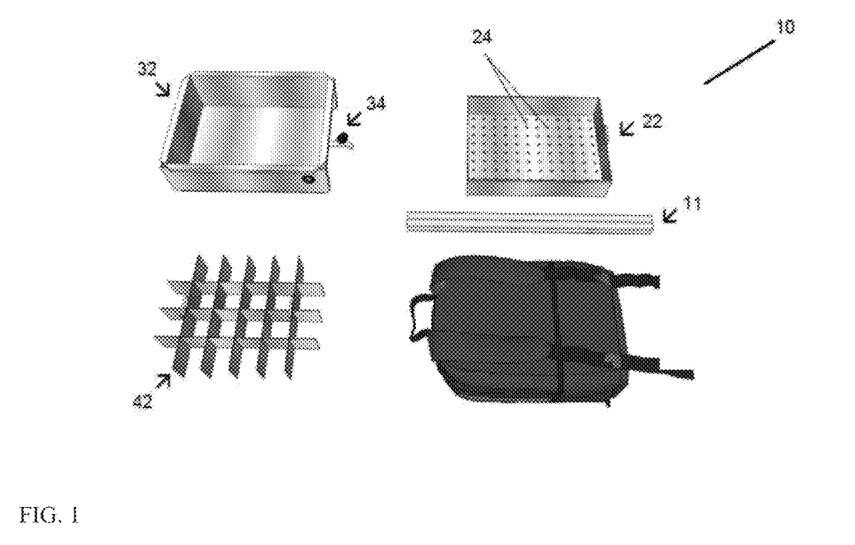
FIG. 1 is a general view of the set that forms the subsampler object of this invention.

The Subsampler in the present invention consists of a set of independent structures: two trays, a separator, and support legs, represented by the number (10) in FIG. 1.

It is worth pointing that the subsampler in the present invention also has a system to measure the correct positioning of the equipment on site and, alternatively, a packaging and transport system as shown in FIG. 1.

The construction of the subsampler structures can be done with any feasible material for a technically minded person. Preferably, the more adequate materials are steel, aluminum, resin, or plastic.

Figure 2A:
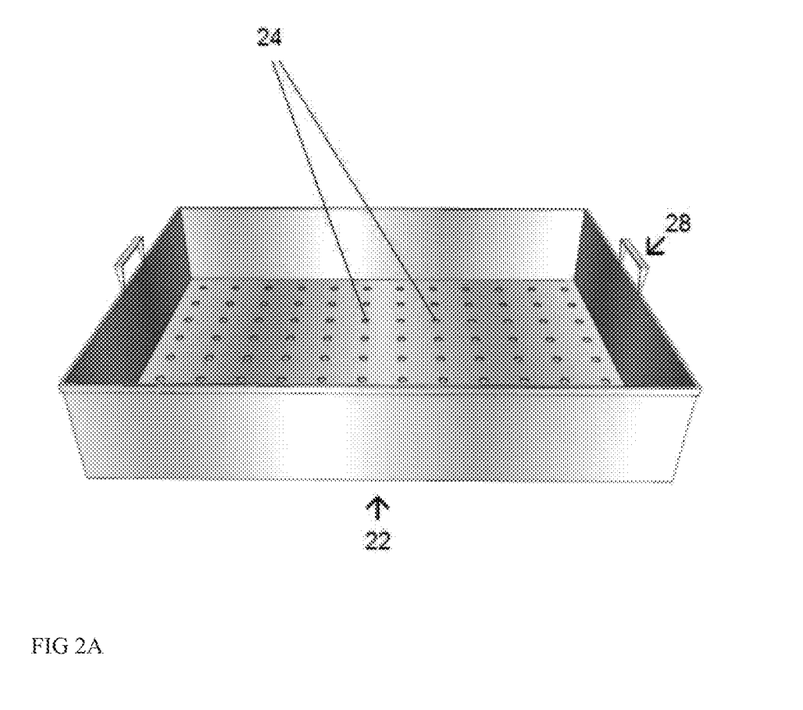
FIG. 2A is a front view of the internal tray.
Figure 2B:
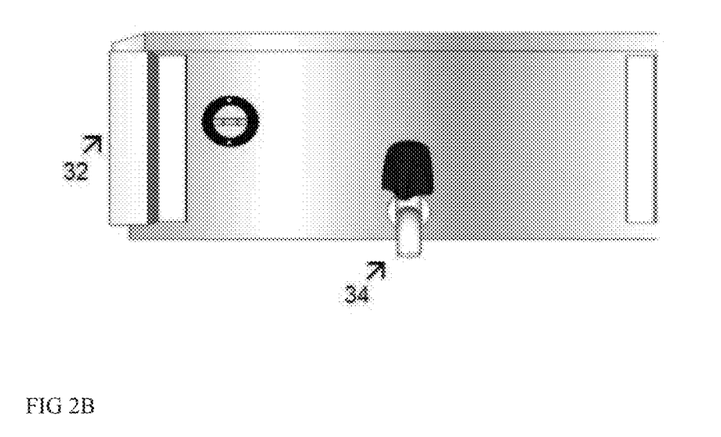
FIG. 2B is a front view of the external tray, for the subsampler shown in FIG. 1.
Figure 3:
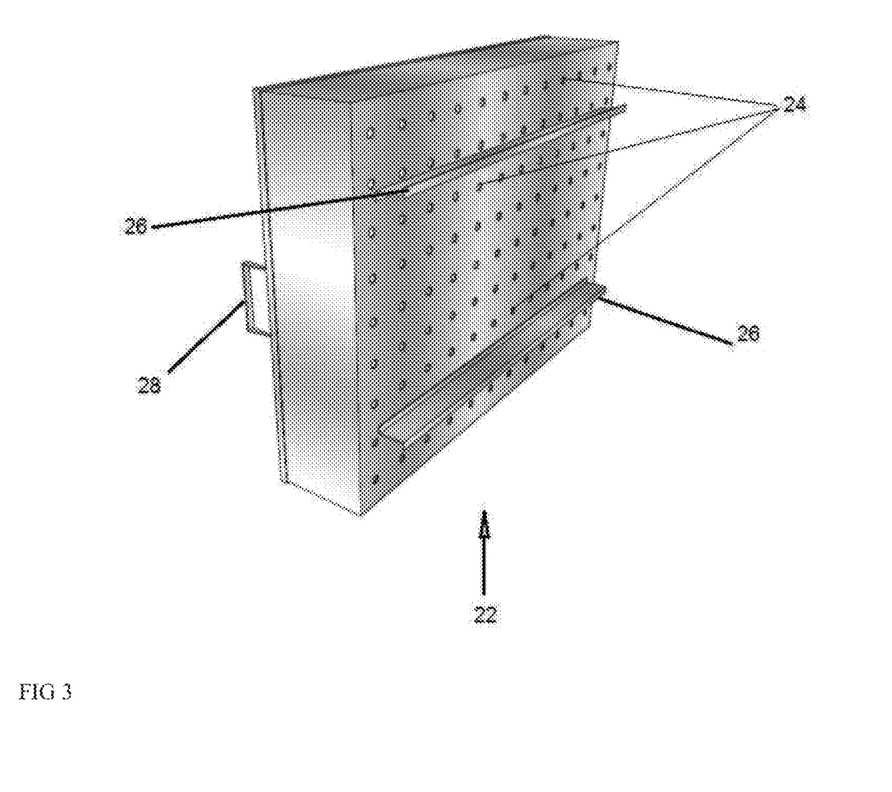
FIG. 3 is a perspective view of the lower part of the internal tray shown in FIG. 2A, showing a support system for the internal tray and the water flow system.

The internal tray (22), shown in FIG. 2A, of size such as to fit the external tray (FIG. 2B), has in its bottom an outlet to discharge water, preferably with holes (24) equally distributed to allow its flow. The said internal tray (22) also has a net (not shown) to filter the biota-sediment complex of size that is adequate to the type of study to be undertaken, that can vary, preferably, from, 500 µm to 1 mm. FIG. 3 shows the outer side of the base of the internal tray (22) where there is a support system (26) in free form. The free form of the support system (26) is chosen so as not to prevent the flow of water, and can be S-shaped, albeit not limited to it, set in a direction parallel to the water flow line, thus jointly avoiding the loss of form of the tray and the flow back phenomenon. There can optionally be the presence of algae (28) in the internal tray (22) to facilitate its handling. (FIG. 2A)

The outer tray (32) with a size adequate to the size of the sample to be collected, preferably ranging from 60×50×16 to 36×36×10 cm, has a reinforcement edge to assist in supporting the weight and shape of the device. Said outer tray (32) has: a water outlet (34) system (such as, but not limited to, a tap or threaded plug). Additionally, the outer tray (32) has a support system with legs and a system for the correct (horizontal positioning of the device in the field. In the preferred configurations of the present invention, possible positioning systems that can be used are those of the 'bubble' or 'pendulum' types, but not limited to them. (FIG. 2b)

Figure 4:
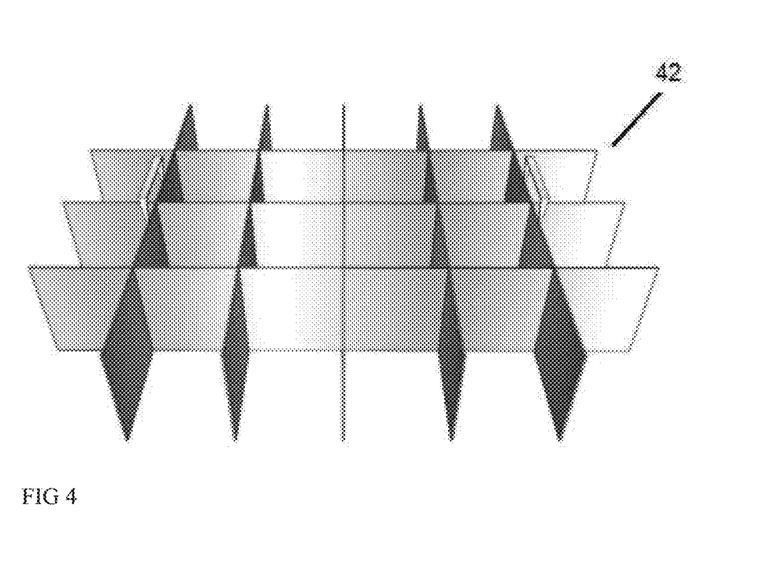
FIG. 4 is a view from the top of the separation system for the subsampler shown in FIG. 1.

The separator system (42) shown in FIG. 4 consists of a set of plates fitted perpendicularly between them with the function of separating the material collected from the substrate. This device is sized according to the inner box in which it should fit snugly, separating the material into 24 quadrats. Optionally, handles can be incorporated to the separation system to facilitate its handling. (FIG. 3)

The support legs (11) form a set of rods that can vary in number, provided it is not smaller than four, with height according to ergonomics principles, preferably 80 cm long, but without limiting themselves to this, and can also be adjustable or folding to facilitate the transport of the equipment. According to what is proposed in this invention, the use of support legs (11) is optional and there is no need when the subsampling is done in a laboratory.

Thus, in a preferred configuration of the invention, the subsampler, unlike the others found in the state-of-the-art is used directly on site.

For the perfect operation of the subsampler in this invention it is positioned horizontally at the place of collection, adjusting its legs (11) correctly with the aid of the positioning system. After that, the internal tray (22) is inserted in the external tray (32). The biological material from the collected substrate is stored in the internal tray (22) and covered with the river water. Large-sized sticks, stones, and leaves are manually removed by operators, for a standard length of time that ranges from 10-20 minutes. Following this work, part of the water is removed with the opening of the water outlet (34) as found in the outer tray (32); part of the water is removed, and some of it is left still on the bottom of the inner tray (22).

After that, the water that remains in the tray is added with an adequate amount of anesthetic in proportion to the box used. The anesthetic used in the present invention should be reversible, to allow the survival of the biota that is not used in the later stages of the subsampling. in a preferred configuration of this invention the anesthetic used is gaseous water. However, other reversible anesthetics known in the state-of-the-art can be used in this invention. To facilitate the understanding, the preferred proportion is of two liters for a 60×50×16 box filled with 10 cm of water. This procedure aims at anesthetizing the animals found in there, thus ensuring a homogeneous distribution of the biota in the subsampler. After the time necessary for the anesthetic to act, all the material is mixed in the inner tray (22). In the case where gaseous water is used this stage can last from 5 to 15 minutes.

After the homogenization operation the separator system (42) is positioned on the tray. The water outlet (34) is opened until the full removal of the anesthetic solution from the subsampler. By means of a draw, according to the methodology chosen, quadrats from the separator (42) are selected and the material in them is removed. It is recommended and preferred that a draw is made of 4-6 of the 24 quadrats. After that, the material found in the selected quadrats is removed. The samples collected are stored in proper containers such as, but not limited to, plastic bags and immobilized. The immobilization can be done with the use of organic compounds such as, but not limited to, 70% to 80% concentrated alcohol; 4% to 10% formaldehyde, or a blend of both, for the transport to the laboratory where the identification of the specimens will be made.

The material remaining in the inner tray is returned to the water environment.

The subsampler in the present invention has clearly shown to be, through its onsite use, that it allows for a rapid subsampling of the material collected.

According to what is proposed in this invention, subsampling with the equipment and the use of the methodology described produces, apart from optimizing the time spent, a series of advantages when compared with the equipment and methodologies found in present-day state-of-the-art.

Considering a river with trees on its banks, with many leaves at its bottom, by using the subsampler of the present invention a considerable reduction in the volume of the material can be achieved. When comparing this point to what is presently the state-of-the-art it is possible to get a ⅔ approximate reduction of the volume of the material washed in the field and, after washing, a ¾ reduction. Apart from that, with the present invention, one avoids the washing stage of the biological material at the laboratory, a stage that requires considerably high investment in time.

As regards the transportation and preservation under conserving agents, the use of the subsampler in the present invention cuts some 80% of the volume of the material collected when compared to the state-of-the-art, that is, with classical subsampling.

The use of this equipment and its methodology contribute more effectively for the preservation of the integrity of macroinvertebrates when compared to other subsamplers found in the state-of-the-art, which consequently allows for the execution of better taxonomic separation and tagging. This feature is produced as a result of the homogenizing system for the material found in the inner tray. In the subsampler of the present invention the material is collected along with a large amount of water and with the specimens still alive, unlike other techniques where the homogenizing is done in dry conditions in the laboratory, and with specimens previously fixed in alcohol. This causes the hardening of the muscle tissues, favoring damage to the animals.

The homogenizing proposed by the present invention also contributes significantly to the randomizing of the organisms, i.e. favoring their random distribution along the quadrats.

Another difference related to the state-of-the-art is found in relation the biota that is left in the on-site subsampler. This biota usually consists of thousand of larvae and adults from dozens of different taxonomic groups. According to the present invention these organisms are returned to ecosystem while they are alive. Therefore, once in contact with the environment's water (river) the anesthetic effect of the gaseous water, for example, is instantly reversed.

The invention presented here can be considered environmentally friendly, affecting minimally the location where the collection is made, apart from being very efficient; reducing operating time frames, as well as costs and, on the other hand, maintaining the random nature/wealth of the species, factors that are fundamental in water biomonitoring programs.

Despite the use of the subsampler in the present invention being preferably of a on-site nature, the scope of the invention includes its use also in a laboratory environment, fully assembled or on a benchtop, without its legs, to allow the subsampling of material previously fixed in the field.

Below are listed configurations for the present invention, and we point that it is not limited to the examples below but also includes variations and modifications, within the limits of its operation.

EXAMPLES

Example 1

Subsampler Assessment

Organism Collection

In order to evaluate the efficacy of the subsampling done by the equipment and the methodology in the present invention the data of 6 water streams, considered lightly affected areas, was used. The streams are located in the basins of rivers Macacu and Guapimirim, a dense ombrophilous forest area belonging to the domains of the Atlantic Forest Range, in Sea Range, state of Rio de Janeiro (Table 1). The criteria to define the reference areas were at first: visual habitat evaluation protocol with either excellent or good condition; over 75% of the basin area above the point under forest cover; Dissolved Oxygen over 6 mg/L; Fecal Coliform per 100 mL<10.

The collection procedure considered samplings of the multi-habitat kind in a collection proportional to the availability of the substrate in the river section studied. A kick sampler was used with a 500-micron mesh, with a total 20 replicas per point where each one consists of 1 (one) m² of substrate surveyed. Thus, some 20 m² of substrate in the river were collected. The sample was unified and kept in ethanol at 80%. In the 6 water streams studied the collection was done by the same team and the maximum standardization was sought for the procedure.

TABLE 1

Characterization of the collection points

| Rivers | Code | Order | Altitude (m) | Visual Evaluation Protocol |
|---|---|---|---|---|
| River Andrew | A | 2 | 930 | Excellent |
| River Soberbo | B | 3 | 100 | Excellent |
| River Manoel Alexandre | C | 4 | 80 | Excellent |
| River Iconha | D | 1 | 1220 | Excellent |
| Macacu Branch River (River Placa) | E | 1 | 1100 | Good |
| River Gato | F | 3 | 90 | Good |

Subsampling Procedure

In this configuration of the present invention the subsampling was done per area and, for that, a subsampling apparatus was used, split into 24 quadrats sized 64×36 cm.

The apparatus consists of two plastic trays (inner and outer) fit in such a way as previously described.

The inner tray (22) as shown in FIG. 2A has holes evenly distributed at the bottom and a 500 μm mesh (equal to that of the sampler). On its outer side there is a S-shaped support system in a direction parallel to the water flow line.

As for the outer tray (32) used in this analysis, it consists of a tray for the water flow with a tap on the side, also with the 'bubble-type' correct positioning system, as already demonstrated.

The separator system used, according to FIG. 4, consists of a set of plates fitted in a perpendicular manner so to fit snugly into the outer tray (22), to separate the material into 24 quadrats. The handles found in the separator system facilitated the handling of this part of the equipment.

The samples were washed in the laboratory, in the internal tray (22) of the subsampling equipment to remove the coarser material such as large leaves and sticks. After that, the inner tray was filled with some 15 liters of water and the material was homogenized for 5 minutes to ensure the even distribution of the entire sample on the tray surface. The tap (34) was then opened and the water flowed in a homogeneous way to the outer tray (32). The separator (42), with its 24 aluminum quadrats was then fitted onto the inner tray (22). The material corresponding to each quadrat was removed and individualized in a plastic bag.

This procedure was repeated for the 6 sampling points, resulting in 144 (24×6) plastic bags, corresponding to 144 quadrats. Each quadrat was then screened to exhaustion and the organisms identified as per genera (except Lepidoptera and Diptera that were tagged as per family) with the aid of a stereoscope microscope. Considering that each river sample represents 20 m² of substrate, each quadrat then equals 0.83 m² and approximately 4.2% of the total sample. We took into account the processing time (screening and tagging) for each quadrat to ascertain the gain in terms of time and consequently the resources saved in the subsampling procedure.

The similarity analysis done showed that the communities with 4 quadrats already display high similarity values with the total 24-quadrat sample based on the 3 indices used and the standard deviations under 0.01. For the Morisita Index, even the smaller-size subsample has a 98% similarity with the total sample. The Bray-Curtis Index displayed the smallest similarity values but pointed that a 4-quadrat subsample already has a 70% similarity with the total sample.

The results of the previous analyses show then that the macroinvertebrate community found in 6 quadrats is similar to that found in the full 24-quadrat sample in terms of structure and composition.

Example 2

Organism Distribution Analysis

Randomness Verification

In order to test whether the taxa subsampled, as per Example I, have a random distribution in the quadrats, a test was done based on the Dispersion Index (Krebs, C. J. 1998. Ecological Methodology. Benjamin/Cummings, Menlo Park.). The dispersion index is calculated through the ratio between the observed variance and average. A bivariate Chi-square test is then applied, considering the null hypothesis that the data follows the distribution of Poisson. The $X^2$ is calculated through the multiplication of the value of the dispersion index by the number of freedom degrees (n−1).

Figure 5:
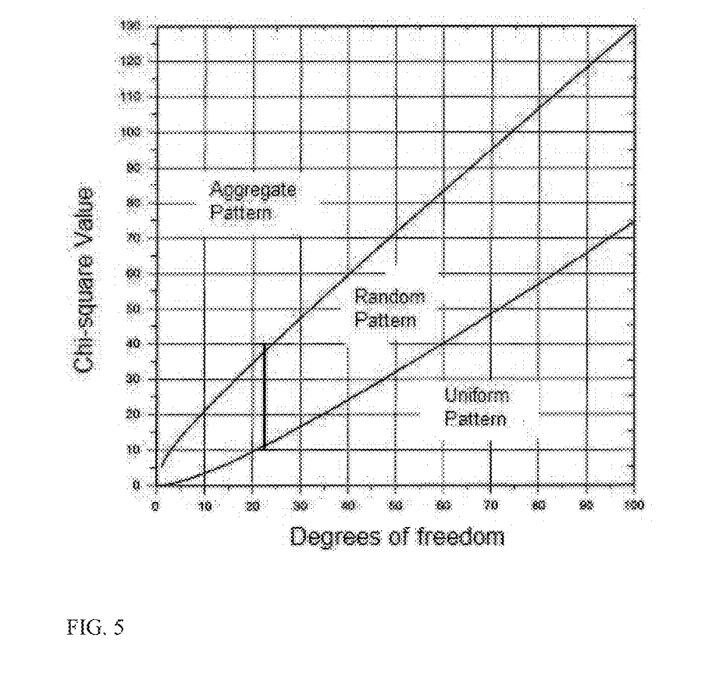
FIG. 5—Critical values for the Chi-square test for the Dispersion Index for $\alpha=0.05$ and $n<101$.

There are two possible directions for deviation. If the organisms are evenly distributed the variance will be much smaller than the average and the Dispersion Index will be close to zero. If the organisms were clustered the variance observed would be greater than the average and the Dispersion Index would be much higher than 1 (one)(Krebs, C. J. 1998. Ecological Methodology. Benjamin/Cummings, Menlo Park) (FIG. 5). Considering $\alpha=0.05$ and 23 degrees of freedom, the values for $X^2$ in this case should be between 11 and 37 for the hypothesis of random distribution to be accepted. This test was undertaken for all the taxa on a family level, considering the 24 quadrats in the 6 rivers.

It was found that most of the subsampled macroinvertebrate families had a random distribution, similar to that of Poisson in the 24 quadrats. The mean Dispersion Index varied in values a little over 1 in the 6 water streams. The summarized results are in Table 2.

Figure 6:
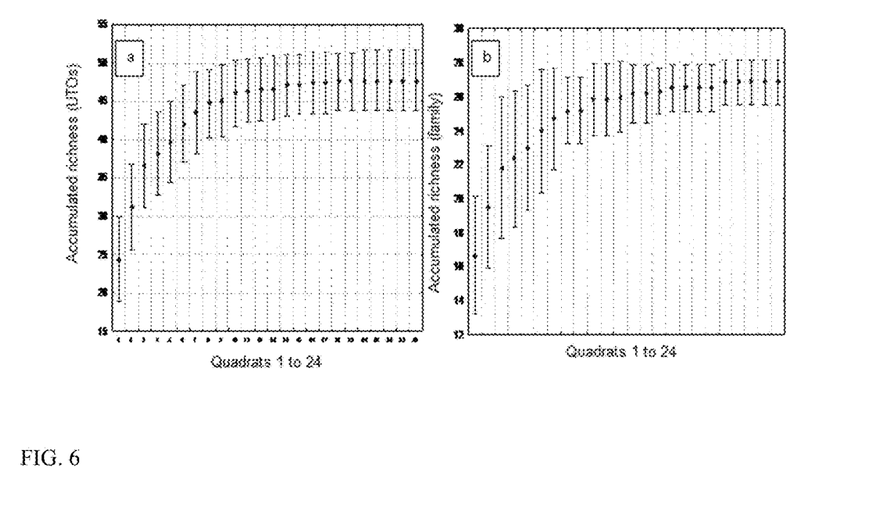
FIG. 6—Curves for environmental effort showing mean and standard deviation for the 6 points sampled: (a) wealth accumulation in UTOs and (b) wealth accumulation in families.

It was also found that the abundances were different between the points and that implies different wealths with their increase as a result of the number of organisms in the sample—FIG. 6b.

The rarefaction curve produced considered communities with 100 to 1,600 organisms in the 6 sampling points. The result of the analysis is in FIG. 2 where it is possible to see

TABLE 2

Distribution of abundances and wealth in quadrats for the 6 rivers surveyed.

|  | River Andrew | River Soberbo | River Manoel Alexandre | River Iconha | River Placa | River Gato | Averages |
|---|---|---|---|---|---|---|---|
| Total Abundance | 2435 | 2193 | 2722 | 2663 | 1684 | 1939 | 2272.667 |
| Mean abundance per quadrat | 101.4583 | 91.375 | 114.125 | 110.9583 | 70.16667 | 80.79167 | 94.81249 |
| Standard Deviation | 24.92769 | 20.16845 | 27.81978 | 28.95045 | 20.36977 | 18.15867 | 23.39914 |
| Mean abundance in 4 quadrats | 421 | 405 | 485 | 482 | 295 | 319 | 401.1667 |
| Mean abundance in 6 quadrats | 709 | 595 | 770 | 699 | 434 | 479 | 614.3333 |
| Mean abundance in 8 quadrats | 890 | 777 | 994 | 926 | 562 | 603 | 792 |
| Mean abundance in 12 quadrats | 1332 | 1117 | 1413 | 1345 | 839 | 909 | 1159.167 |
| Total wealth (UTOs) | 57 | 52 | 61 | 58 | 45 | 50 | 53.83333 |

Thus, the subsampling procedure and apparatus in the present invention ensured the random distribution of the organisms. This was driven mainly by the methodology described herein, which avoids to the maximum that the organisms are not sampled due to a flaw in the sample homogenization procedure.

Example 3

Evaluation of Taxa Wealth

Determination of Effort Required

It is worth pointing out that the on-site sampling should be representative of the heterogeneous character of existing habitats and should be a standard procedure to endure the degree of comparison of the results.

In order to prove the efficacy of the equipment and of the methodology of the present invention as regards the representativeness of the taxa, work was done to determine the collector curve, using Operating Taxonomic Units (UTOs), that is, the best taxonomic resolution possible. Work was also done to produce the collector curve for the macroinvertebrate fauna identified only on a family basis.

Figure 7:
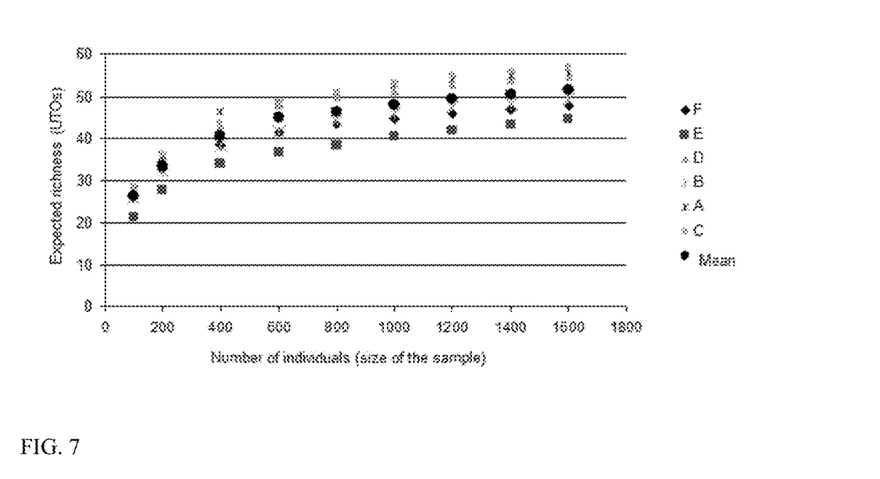
FIG. 7—Wealth expected after rarefaction analysis in differently sized communities in the 6 water streams (A, B, C, D, E, and F) and mean values.

FIG. 6 shows the curves obtained and shows the averages and the standard deviation for accumulated wealth in each quadrat for the 6 rivers. It is possible to visually verify that, from the sixth quadrat the accumulated wealth starts to display a stabilizing trend, as per FIG. 6a.

the absolute values in the expected wealths, for each water stream, for each sample size. The black circle line shows the averages. Given that the mean abundance of 6 quadrats was of 614 individuals one can consider then that 600 individuals equal 6 quadrats. Another point to highlight is that the adding of 1,200 individuals to the sample (from 400 to 1,600) led to an mean increase of 10 UTOs.

Thus, for the example at hand, it was determined that the use of 6 quadrats, which add to 25% of the sample and represent around 5 m$^2$ of substrate from the sampled river, it was enough for the application in biomonitoring programs when using the equipment and the methodology of the present invention. That is, the results showed that the macroinvertebrate community found in 6 quadrats is quite similar to the community found in the total 24-quadrat sample.

And moreover, the equipment as well as the methodology of this invention were capable of producing robust data for the biological evaluation, comparing different impact intensity areas. Overall, this is the most important test as it directly evaluates the efficiency in sample size as it differentiates the areas affected from the reference areas.

Example 4

Size of Subsample and Metrics

The analysis done to assess the direct effect of subsample size on the values of biological measurements that might form a multimetric index took place via the definition of sub-communities with 4, 6, 8, 12, and 24 quadrats. The results were presented through Box plots considering the medians and the 25-75% percentiles of the metrics values in the 6 water streams, in each one of these randomly generated sub-communities. A test was then done to compare the value of the metrics for a given subsample size (4, 6, 8, or 12) with the total sample (24 quadrats).

The metrics chosen for the analysis of the subsampling as done by the equipment and methodology described in Example I were: wealth, relative abundance, trophic groups, and tolerance. FIG. 8 presents the assessment of the values of these metrics in the different subsample sizes.

Figure 8A:
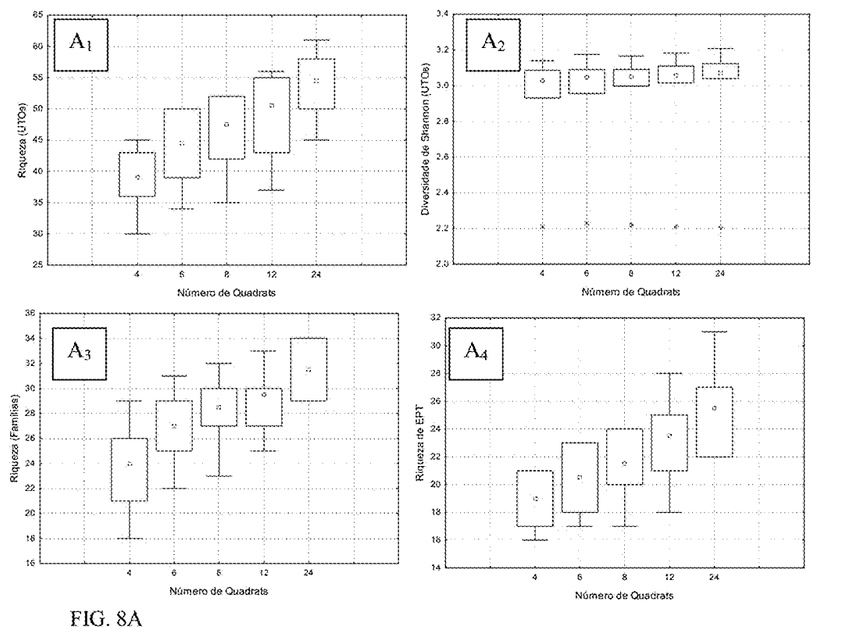
FIG. 8—Assessment of the variation in values for metrics amongst different subsample sizes: (a) metrics on wealth and diversity, (b) composition metrics, (c) trophic metrics, and (d) tolerance metrics.

As regards the metrics that measure just wealth (family total and of Ephemeroptera/Plechoptera/Trichoptera), these seem to be the most affected by the size of the subsample, as the difference between the value of the metrics to 4 and 24 quadrats is significant through the Mann-Whitney test, as shown in FIG. 8a. As for Shannon's Diversity it did not seem affected by it, and produced no meaningful difference.

Figure 8B:
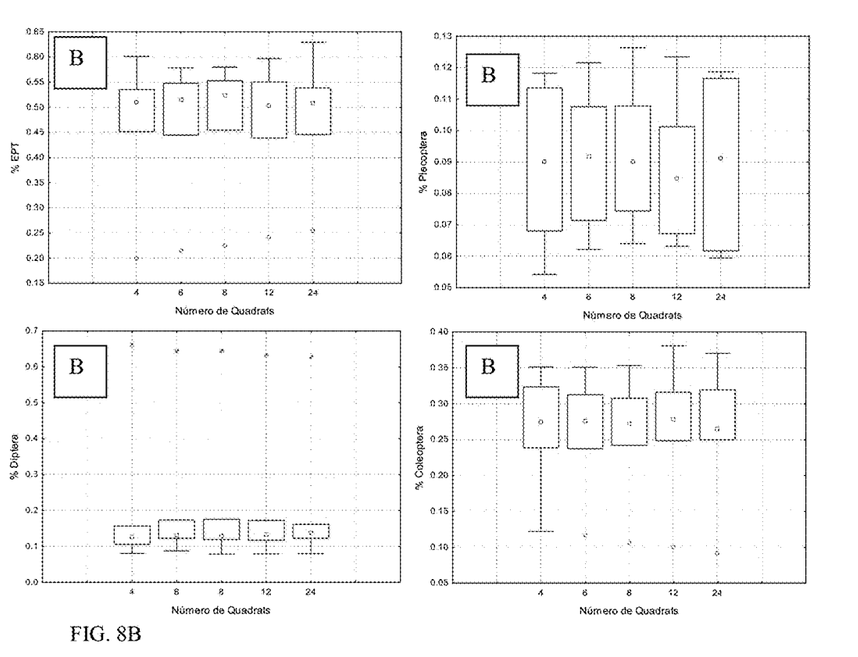

In the case of the metrics for relative abundance, % EPT, % Diptera, % Choleoptera and % Plecoptera were shown to be stable throughout the different subsample sizes, with no significant variation between them, as it can be seen in FIG. 8b. This shows, in an indirect manner, that the sample was well distributed along the tray; it once again shows that the equipment and methodology proposed in the present invention can correctly homogenize the material collected.

Figure 8C:
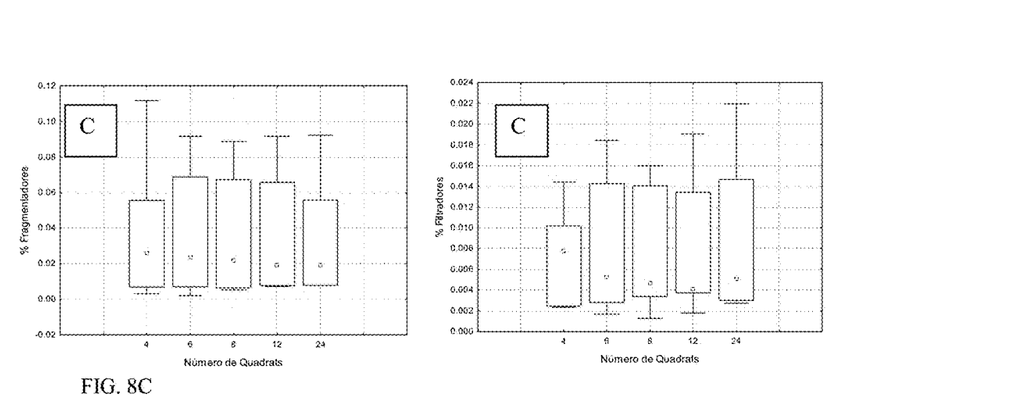

FIG. 8c shows data for the metrics on trophic groupings that correspond to the abundance of theses functional groupings in relation to total abundance (% Filtering Elements and % Fragmenting Elements). Both groupings displayed stability in their values, for the different subsample sizes, demonstrating that the proportion of these organisms is kept, independently from subsample size.

In the case of the metrics to evaluate tolerance, two were studied: IBE-IOC and the Baetidae/Ephemeropter measurement.

The first one, IBE-IOC, is a biotic index based on the tolerances of the different genera and families of benthic macroinvertebrates; being, on its own an evaluation tool, providing a classification of the place of collection in categories of different impact levels. A sample error that produces a loss of sensitivity in the index may then mean an error in evaluation and mislead the necessary handling measurements. This index ranges from 0 to 15 and the higher it is the better the biological integrity of the place is, being considered as a measure of integrity. The fact that it was, in the comparative analysis between reference areas, intermediate areas and affected areas, sensitive to a 6-quadrat family points at the fact that this subsample size does not affect a sensitivity of this tool. And, from 6 quadrats on the community already gets grades that are quite similar to those of the index. Only the 4-quadrat subsample produced a significant difference.

The Baetidae/Ephemeroptera measurement is also a direct measurement for tolerance as it measures the relation between the most tolerant family of the Ephemeroptera and the total abundance of the order. No significant difference was observed amongst all the relative abundance measurements, amongst the different subsample sizes, according to FIG. 8d.

This way, it is found that both the equipment and methodology described in Example I have the accuracy and precision needed for the establishment and analysis of the metrics required for the biomonitoring of water systems.

Example 5

Similarity Analysis in Terms of the Composition and Structure in the Different Sizes of Subsamples The analysis of similarity done used three assessment indices: Morisita, Bray-Curtis, and Sorensen. FIG. 8 describes the mean similarity with the total sample in growing size subsamples, with standard deviations not being pointed in the graphs of the Figure as they were all under 0.01.

Figure 8D:
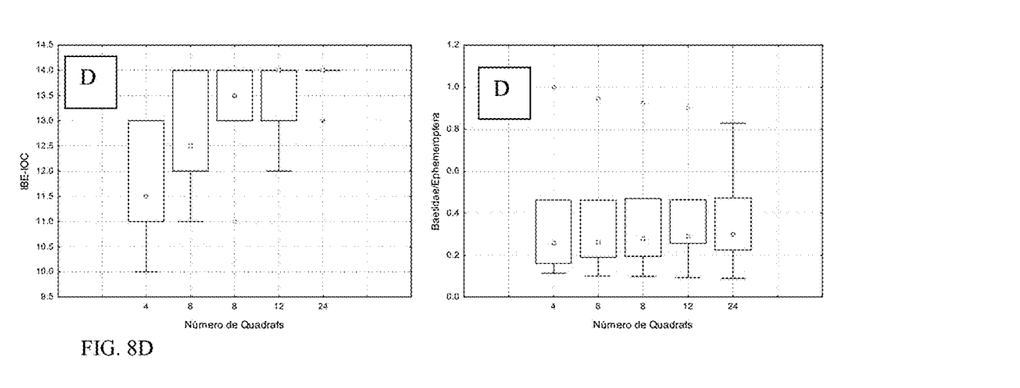

The communities with 4 quadrats already displayed high similarity values when compared to the total 24-quadrat sample by the three indices used. For the Morisita Index, (Morisita 1959), even the smaller-size subsample has a 98% similarity with the total sample). The Bray-Curtis Index (Bray & Curtis, 1957) displayed the smallest similarity values but pointed that a 4-quadrat subsample already has a 70% similarity with the total sample (FIG. 8d).

Figure 9:
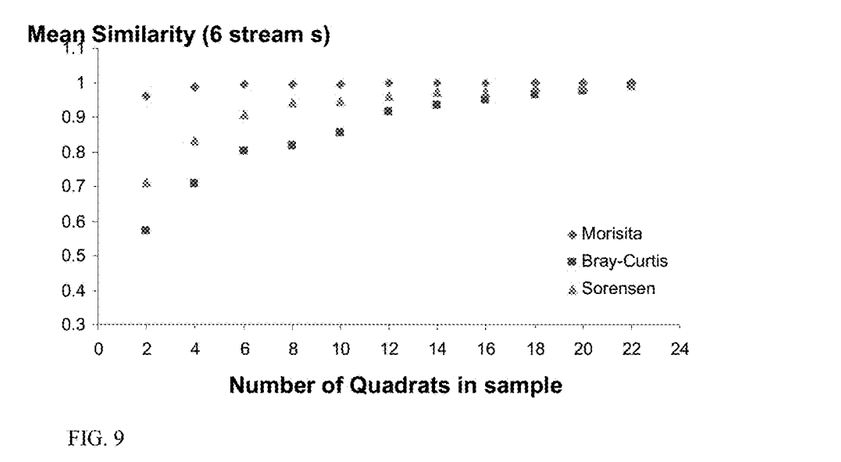
FIG. 9—Mean similarity values with total sample (24 quadrats) in growing size subsamples.

The analysis of the sampling effort curve points that, in operating taxonomic units, the accumulation of wealth is no longer significant in 6 quadrats. All the metrics, including those of taxa wealth, have similar values in samples sized from 6 quadrats. The analysis of similarity pointed that 4-quadrat samples have high similarity values with 24-quadrat samples, as shown in FIG. 9.

All this information demonstrates that a community found in 6 quadrats is quite similar to that found in the total 24-quadrat sample, both as regards structure as in wealth and its composition.

Example 6

Subsample Size Validation

In order to test whether a 6-quadrat can actually serve as a basis for a biomonitoring program a direct comparison was made between the 6 reference areas considered in this evaluation, as per Example I and 6 intermediate and strongly affected areas of independent data sets. The evaluation of the seriousness of the impact was made through a visual habitat protocol modified to attend to the realities of the Brazilian people, assessing the state of conservation of the river bed and of its banks, and of physical and chemical analyses (dissolved oxygen, pH, nitrites, nitrates, phosphates).

The comparison was made via the calculation of 4 direct impact measurements that are often included in multimetric indexes or represent, on their own, a non-index. A Mann-Whitnney test was undertaken to ascertain the significance of the difference and to confirm if there is a distinction between different impact classes.

Figure 10:
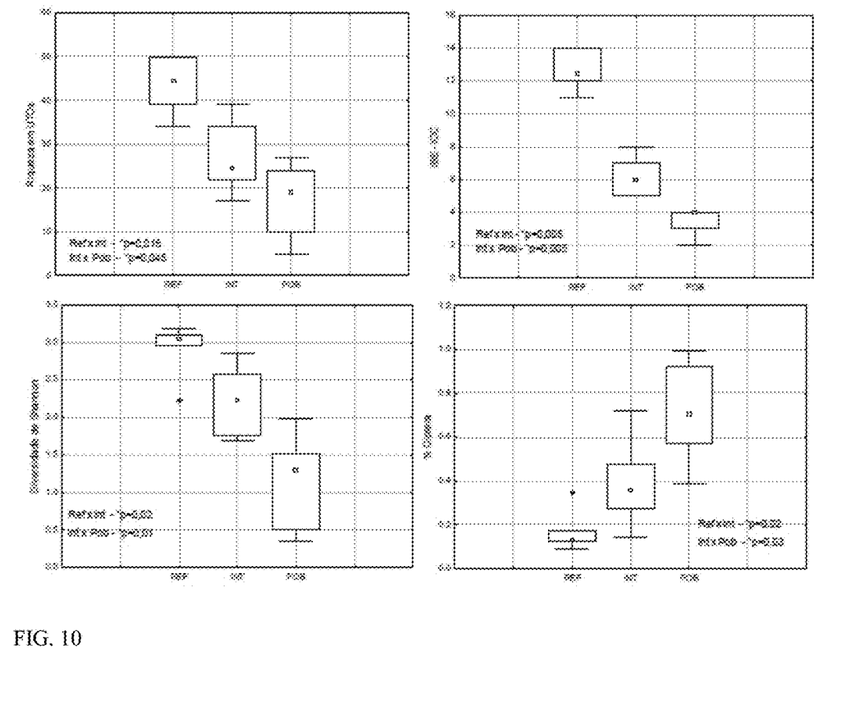
FIG. 10—comparison between measures for impact measures (metrics) using the community found in 6 quadrats in areas minimally affected (REF) with average intensity disturbances (INT) and strongly altered (POB).

FIG. 10 describes a comparison between values for impact measures (metrics) using the community found in 6 quadrats in areas minimally affected (REF) with average intensity disturbances (INT) and strongly altered (POB). The four assessing measurements considered displayed a high sensitivity to detect the differences between the impact classes. Even in the intermediate class which many times displayed subtle disturbances, it was differentiated by the 6-quadrat community.

Example 7

Subsampling Time

In this configuration of the invention if only one person undertakes the processing to subsample the sample collected according to Example I, a 6-quadrat subsampling will result in a 12-hour saving in the processing of a sample with a minimally affected area.

It should be pointed that the loss of a few taxa, inherent to any subsampling technique, in the present invention, brought practically no change to the generation and functioning of the metrics of an index, guaranteeing the scientific robustness of the tool to assess the ecological integrity of the water streams studied.

All the results presented in the examples above show that the subsampling procedure, done with the equipment and methodology of the present invention allows their application in the biomonitoring of water systems, ensuring especially scientific rigor in the obtaining of the multimetric indices.

The invention claimed is:

1. An apparatus for subsampling water macroinvertebrate comprising:
   a) an external tray comprising:
      i) a reinforcement edge adapted to assist in supporting a weight of the apparatus and keeping a shape of the apparatus;
      ii) a water outlet system;
      iii) an S-shaped leg support system arranged in parallel to a water flow line so as to jointly avoid a loss of tray shape and a backflow phenomenon; and
      iv) a system adapted for correctly positioning the apparatus, wherein the system is of a bobble or pendulum type;
      v) a net to filter biota and sediment, wherein the biota and sediment filter net is sized from 500 μm to 1 mm;
   b) an internal tray comprising:
      i) a drainage system comprising a water drain outlet with holes equally distributed on a base of the apparatus;
      ii) a support system; and
      iii) a separator formed by quadrats comprising a set of plates that fit each other in a perpendicular manner, with 24 quadrants sized according to the internal tray in which they are to fit perfectly, and wherein the internal tray fits into the external tray.

2. The apparatus according to claim 1, wherein the water outlet system is equipped with a tap or threaded cap.

3. The apparatus according to claim 1, wherein the leg support system is adapted to receive legs comprising rods that can vary in number, provided they are not less than four, being optionally adjustable or folding.

4. A method for subsampling water macroinvertebrates using the apparatus of claim 1, said method comprising the steps of:
   a) correctly positioning the apparatus on a surface,
   b) adding to the internal tray a substrate collected in water;
   c) removing large-sized materials;
   d) draining part of the water via an opening of the water drainage system, without fully removing the water;
   e) adding to the apparatus a reversible anesthetic solution comprising gaseous water so that organisms in the apparatus are sensitized;
   f) homogenizing the substrate;
   g) fitting the separator on the internal tray;
   h) opening the water drainage system to release the reversible anesthetic solution;
   i) randomly removing the substrate from 4 to 6 of the 24 quadrats; and
   j) storing the substrate collected in step (i) in a solution adequate for transportation to a laboratory, wherein the solution consists of organic compounds selected from the group consists of an alcohol, a formaldehyde, and mixtures thereof.

* * * * *